US012751626B2

(12) United States Patent
Albrecht et al.

(10) Patent No.: US 12,751,626 B2
(45) Date of Patent: Oct. 6, 2026

(54) METHOD FOR IDENTIFYING A REGION OF A TUMOUR

(71) Applicant: CARL ZEISS MEDITEC AG, Jena (DE)

(72) Inventors: Christian Albrecht, Aalen (DE); Marco Wilzbach, Aalen (DE)

(73) Assignee: CARL ZEISS MEDITEC AG, Jena (DE)

( * ) Notice: Subject to any disclaimer, the term of this patent is extended or adjusted under 35 U.S.C. 154(b) by 872 days.

(21) Appl. No.: 17/794,721

(22) PCT Filed: Jan. 21, 2021

(86) PCT No.: PCT/EP2021/051360
§ 371 (c)(1),
(2) Date: Jul. 22, 2022

(87) PCT Pub. No.: WO2021/151780
PCT Pub. Date: Aug. 5, 2021

(65) Prior Publication Data
US 2023/0074634 A1 Mar. 9, 2023

(30) Foreign Application Priority Data
Jan. 31, 2020 (DE) ..................... 10 2020 102 476.2

(51) Int. Cl.
*A61B 5/00* (2006.01)
*A61B 90/00* (2016.01)
(Continued)

(52) U.S. Cl.
CPC .......... *A61B 5/0071* (2013.01); *A61B 5/0075* (2013.01); *A61B 5/0084* (2013.01);
(Continued)

(58) Field of Classification Search
CPC ........ A61B 5/0059–0097; A61B 90/20; A61B 2090/306; A61B 2090/373; A61B 2090/3735
See application file for complete search history.

(56) References Cited

U.S. PATENT DOCUMENTS 7,580,185 B2 * 8/2009 Haisch ................. G02B 21/365 359/372
8,189,201 B2 * 5/2012 Haisch ................. G02B 21/368 356/497
(Continued)

FOREIGN PATENT DOCUMENTS

CN 101461706 A 6/2009
CN 103608662 A 2/2014
(Continued)

OTHER PUBLICATIONS

Written Opinion for Application No. PCT/EP2021/051360, mailed Jun. 16, 2021 (14 pages).
(Continued)

*Primary Examiner* — Angela M Hoffa
(74) *Attorney, Agent, or Firm* — NIXON PEABODY LLP; Jeffrey L. Costellia

(57) ABSTRACT

The invention relates to a computer-implemented method for identifying a region (21) of a tumour (23) in a tissue-field image (27), which image shows a tissue region (25) having a tumour (23) and has been obtained by means of light reflected or emitted by the tissue region (25). In the method, the region (21) of the tumour (23) in the tissue-field image (27) is identified on the basis of a characteristic value for the intensity of at least one component of the light reflected or emitted by the tissue region (25). The characteristic value is determined using the intensity of the at least one component in an image detail of the tissue-field image (27), which
(Continued)

image detail corresponds to a tissue portion (36, 36') of the tissue region (25) at which at least one piece of histological information was obtained.

22 Claims, 7 Drawing Sheets

(51) Int. Cl.
*A61B 90/20* (2016.01)
*A61B 90/30* (2016.01)

(52) U.S. Cl.
CPC .............. *A61B 90/20* (2016.02); *A61B 90/37* (2016.02); *A61B 2090/306* (2016.02); *A61B 2090/373* (2016.02)

(56) References Cited

U.S. PATENT DOCUMENTS

| | | | | |
|---|---|---|---|---|
| 8,300,309 | B2 * | 10/2012 | Haisch | G02B 21/18 356/498 |
| 8,320,996 | B2 * | 11/2012 | Panasyuk | G01N 21/21 600/407 |
| 8,705,042 | B2 * | 4/2014 | Haisch | G01N 21/3563 356/456 |
| 8,810,907 | B2 * | 8/2014 | Haisch | G02B 21/365 359/388 |
| 9,044,142 | B2 * | 6/2015 | Hauger | A61B 1/043 |
| 9,241,636 | B2 | 1/2016 | Koizumi et al. | |
| 9,625,387 | B2 | 4/2017 | Demos et al. | |
| 9,921,406 | B2 | 3/2018 | Wang et al. | |
| 10,054,775 | B2 | 8/2018 | Hauger et al. | |
| 11,154,199 | B2 * | 10/2021 | Hendriks | A61B 5/0066 |
| 11,602,398 | B2 * | 3/2023 | Regensburger | A61B 34/20 |
| 11,944,450 | B2 * | 4/2024 | Yaroslavsky | A61B 5/0075 |
| 2004/0109231 | A1 * | 6/2004 | Haisch | G01N 21/6428 359/385 |
| 2004/0152987 | A1 | 8/2004 | Haisch | |
| 2004/0167742 | A1 | 8/2004 | Haisch | |
| 2004/0208390 | A1 | 10/2004 | Jiang et al. | |
| 2006/0247514 | A1 | 11/2006 | Panasyuk et al. | |
| 2008/0013166 | A1 * | 1/2008 | Haisch | G02B 21/22 359/372 |
| 2008/0132805 | A1 | 6/2008 | Heywang-Koebrunner et al. | |
| 2010/0097618 | A1 * | 4/2010 | Haisch | A61B 5/0086 356/630 |
| 2010/0143258 | A1 | 6/2010 | Sood et al. | |
| 2010/0157308 | A1 | 6/2010 | Xie | |
| 2010/0208955 | A1 * | 8/2010 | Mehes | G01N 21/6458 382/128 |
| 2010/0254586 | A1 | 10/2010 | Fanenbruck | |
| 2011/0168914 | A1 * | 7/2011 | Haisch | G02B 27/0172 356/479 |
| 2011/0280810 | A1 | 11/2011 | Hauger et al. | |
| 2012/0194663 | A1 * | 8/2012 | Haisch | G02B 27/0172 348/E7.085 |
| 2012/0249771 | A1 * | 10/2012 | Haisch | G02B 27/0172 348/79 |
| 2016/0051131 | A1 | 2/2016 | Jeong et al. | |
| 2016/0139391 | A1 * | 5/2016 | Hauger | A61B 5/0071 250/208.1 |
| 2017/0027446 | A1 | 2/2017 | Basilion | |
| 2020/0383733 | A1 * | 12/2020 | Regensburger | G16H 50/20 |
| 2021/0196571 | A1 | 7/2021 | Gaillot et al. | |
| 2021/0251564 | A1 * | 8/2021 | Yaroslavsky | A61B 5/0077 |
| 2023/0218142 | A1 * | 7/2023 | Hauger | A61B 1/000096 600/408 |

FOREIGN PATENT DOCUMENTS

| | | | |
|---|---|---|---|
| CN | 104968257 | A | 10/2015 |
| CN | 107003242 | A | 8/2017 |
| CN | 110167448 | A | 8/2019 |
| DE | 102 52 313 | A1 | 6/2004 |
| DE | 102 52 837 | A1 | 6/2004 |
| DE | 10 2005 033474 | A1 | 1/2007 |
| DE | 10 2009 015598 | A1 | 10/2010 |
| DE | 10 2014 016850 | A1 | 5/2016 |
| DE | 10 2016 117263 | A1 | 3/2018 |
| DE | 1020 18 105 067 | A1 | 9/2018 |
| JP | 2004-202221 | A | 7/2004 |
| JP | 2006-166990 | A | 6/2006 |
| JP | 2015-225346 | A | 12/2015 |
| JP | 2021-501642 | A | 1/2021 |
| WO | 2009/117124 | A1 | 9/2009 |
| WO | 2015/023990 | A1 | 2/2015 |
| WO | WO 2016/201186 | A1 | 12/2016 |

OTHER PUBLICATIONS

Jian et al., "Calibration of fluorescence imaging for tumor surgical margin delineation: multistep registration of fluorescence and histological images", Journal of Medical Imaging, vol. 6, No. 2, Apr.-Jun. 2019, pp. 025005-025005-14.

German Office Action for Application No. 10 2020 102 476.2, dated Nov. 30, 2020, (16 pages).

International Search Report for Application No. PCT/EP2021/051360, mailed Jun. 16, 2021, (6 pages).

Japanese Notice of Reasons for Refusal for Application No. 2022-546116, mailed Jul. 25, 2023 (13 pages).

Office Action in Chinese Patent Application No. 202180011794.X with English Translation, dated Nov. 19, 2025, (62 pages).

May 29, 2026 Chinese Office Action issued in Chinese Application No. 202180011794.X with partial English translation. (7 pp.).

Mar. 13, 2026 Chinese Office Action issued in Chinese Application No. 202180011794.X. (14 pp.).

* cited by examiner

METHOD FOR IDENTIFYING A REGION OF A TUMOUR

CROSS-REFERENCE TO RELATED APPLICATIONS

The present application is the U.S. national stage entry of International Application No. PCT/EP2021/051360, filed Jan. 21, 2021, which claims the benefit of and priority to German Patent Application No. 10 2020 102 476.2, filed Jan. 31, 2020, the contents of which are incorporated by reference herein in their entirety.

The present invention relates to a method for marking a region of a tumor. In particular, the invention relates to a computer-implemented method for marking a region of a tumor in an image of a tissue field, and to a method for producing a processed image of a tissue field with a tumor, in which a region of the tumor is emphasized. Moreover, the invention relates to a computer program for marking a region of a tumor in a provided image of a tissue field, and to a non-volatile computer-readable storage medium having instructions to carry out the computer program. Furthermore, the invention relates to a data processing system which allows a region of a tumor to be marked in a provided image of a tissue field. The invention also relates to a medical apparatus for producing a processed image of a tissue field, in which a region of a tumor is depicted with emphasis.

By way of example, in the case of surgery where brain tumors are intended to be removed, the treating surgeon is faced with the difficult task of striking a balance between the removal of as much pathological tissue as possible and the preservation of as much functional tissue as possible. To simplify the decision regarding the amount of tissue to be removed a number of different intraoperative contrasting methods are available for selection, within the scope of which the accumulation of a fluorescent dye in the tumor tissue simplifies the delimitation of tumor tissue from healthy tissue. An optical surgical system which renders the fluorescence of indocyanine green deposited in tumor cells visible and hence emphasizes the tumor cells is described in U.S. Pat. No. 9,044,142 B2, for example. Methods for emphasizing tumors by means of fluorescent dyes are moreover described in US 2017/0027446 A1 and in US 2010/0143258 A1. In a particularly important method used especially in the case of severe tumors (fast growing malignant tumors) such as glioblastoma, the accumulation of the natural, fluorescent metabolite protoporphyrin IX (PpIX) serves to delimit the tumor tissue from healthy brain regions. In this case, PpIX accumulates in the tumor and is identifiable as a red fluorescent region on a blue background if suitable excitation light and a suitable filter in the observation beam path are used.

However, determining the boundaries of tumor regions is difficult despite using dyes and fluorescence because, for example in the edge region of the tumor, tumor cells infiltrate the surrounding healthy tissue, and hence the edge region is characterized by a decreasing portion of tumor cells in the tissue. Hence, using the example of the PpIX dye, there is a purple or pink region, in which the color transitions from red to blue, between the red region, which marks the tumor tissue, and the blue region, which marks the healthy tissue. In practice, the boundary of the tumor is frequently located in this mixed region where the color transitions from red to blue. However, a variation in the fluorescence of tumor cells of a certain tumor type between different patients and between different tumors cannot be excluded here, as a result of which this type of definition of the tumor boundary is afflicted by a certain amount of uncertainty.

US 2010/0143258 A1 therefore proposes to use a threshold for the intensity of the fluorescence and consider the tissue regions where the intensity of the fluorescence is above the threshold to be tumor tissue and the tissue regions where the fluorescence is below the threshold to be healthy tissue, and to mark the transition from tumor tissue to healthy tissue. US 2010/0143258 A1 does not describe how the threshold is defined.

In relation to the teaching of US 2010/0143258 A1, it is an object of the present invention to provide a method for marking a region of a tumor on the basis of a characteristic for the intensity or for the temporal intensity profile of at least one constituent part of the light emitted or reflected by the tissue region, with the characteristic being able to be determined in advantageous fashion.

In accordance with claim 1 the aforementioned object is achieved by a computer-implemented method for marking a region of a tumor in an image of a tissue field (referred to as tissue field image below) and in accordance with claim 12 the aforementioned object is achieved by a method for producing a processed tissue field image. Moreover, in accordance with claim 19 the object is also achieved by a computer program for marking a region of a tumor in a provided tissue field image, in accordance with claim 20 the object is also achieved by a non-volatile, computer-readable storage medium, in accordance with claim 21 the object is also achieved by a data processing system, and in accordance with claim 22 the object is also achieved by a medical apparatus. The dependent claims contain advantageous configurations of the invention.

According to the invention, a computer-implemented method is provided for marking a region of a tumor in a tissue field image which shows a tissue region with a tumor and which has been obtained by means of light reflected or emitted by the tissue region. The apparatus on which the computer-implemented method is carried out can for example read the tissue field image from a memory, receive said tissue image field via a network, or have said tissue image field input in any other way. In this case, the tissue field image may be received directly from the image-recording apparatus. Within the scope of the present invention, a tissue field image should be considered to be a large-area image which represents an object field of 1 $cm^2$ or more, for example 2 $cm^2$, 5 $cm^2$ or more. The tissue field image may optionally be a magnified representation, with however the magnification not being so high that cellular structures are resolved. Typically, the magnification is in the range from approximately 5× to approximately 40×. In particular, the tissue field image can be an overview image.

In the computer-implemented method according to the invention, the region of the tumor is marked on the basis of a characteristic for the intensity or for the temporal intensity profile of at least one constituent part of the light reflected or emitted by the tissue region, the temporal intensity profile for example being able to be represented by a time constant that characterizes the temporal intensity profile. In this case, marking is implemented by means of electronic image processing. The light reflected or emitted by the tissue region may be in the visible spectral range, in the infrared spectral range or in the ultraviolet spectral range. In particular, the at least one constituent part can be at least one spectral line of fluorescence radiation that is emitted following an excitation by means of a certain excitation light by a dye present in the tissue region.

According to the invention, the characteristic is determined on the basis of the intensity or the temporal intensity profile of the at least one constituent part in an image portion of the tissue field image that corresponds to a tissue segment of the tissue region from which at least one histological information item was obtained. In this case, any information item, in particular any information item on a cellular level, which facilitates the recognition of tissue changes and/or the classification of cells should be considered to be a histological information item. In this case, the image portion of the tissue field image is typically very much smaller than the tissue field image itself and, as a rule, corresponds to less than 1% of the image area of the tissue field image, preferably less than 0.5% of the image area of the tissue field image, and, in particular, less than 0.1% of the image area of the tissue field image. By way of example, the histological information item can be a tumor cell proportion, the oxygen content of the tumor cells, a variable derived from the morphology of the tumor cells, etc.

Consequently, the characteristic is determined in the computer-implemented method according to the invention on the basis of an image portion of the tissue field image which shows a tissue segment for which at least one specific histological information item relating to the respective patient is available. If the histological information item obtained on the basis of the tissue segment is characteristic for a certain part of the region of the tumor, for example for the edge of the region of the tumor, the characteristic determined on the basis of the image portion corresponding to this tissue segment is also characteristic for this part of the region of the tumor. A part of the region of the tumor, for example its edge, can therefore be determined very individually for each patient on the basis of the characteristic determined thus. Therefore, a region of the tumor can be marked by its edge, for example. In this case, the region of the tumor may for example represent that part of the tumor in which the tumor cell proportion exceeds a specified value, for example the value that is intended to mark the edge of the tumor. Alternatively, the region of the tumor may for example represent a part of the tumor in which tumor-specific properties, for instance the pH value, the oxygen content, the concentration of $H_2O_2$ or other oxygen derivatives, etc., are above or below a certain limit. In this case, the course of the edge of the respective region, for example, can be deduced with the aid of the histological information item.

By way of example, the histological information item may be obtained by means of a rapid section histology. Alternatively, however, it may also be contained in particular in a histology image recorded at the image portion of the tissue field image. By way of example, a histology image can be recorded with the aid of a confocal endomicroscope, with the aid of optical coherence tomography (OCT), or with the aid of probes with biosensor-type measurement function. By way of example, it is possible in this case to select, on the basis of the histological information item, a suitable tissue segment in which the intensity or the intensity profile of the light emitted or reflected thereby is representative for a part of the region of the tumor of the respective patient, or in which the intensity or the intensity profile of the light reflected or emitted thereby forms a suitable starting point for calculating an intensity of the reflected or emitted light, which is representative for the part of the region of the tumor of the respective patient.

In a first variant of the computer-implemented method according to the invention, the characteristic is determined by virtue of at least one histology image being displayed and a selection function for selecting a selected histology image from the displayed histology images being provided, following the actuation of which an actual intensity value or an actual temporal intensity profile is determined for the image portion that shows the tissue segment at which the selected histology image was recorded. The determined actual intensity value or the determined actual temporal intensity profile is then defined as a characteristic for the intensity or the temporal intensity profile of the at least one constituent part. If the selected histology image was for example recorded at the edge of the region of the tumor, the determined actual intensity value or the determined actual temporal intensity profile is characteristic for the edge of the tumor, and so the edge of the region of the tumor can be marked on the basis of the determined actual intensity value or the determined actual temporal intensity profile.

Instead of making the selection on the basis of the histology images, there is the option of processing the at least one histological information item contained in the histology image for at least one histology image and of displaying the processed histological information item for each histology image. A selection function for selecting a selected processed histological information item from the displayed processed histological information items then is provided, following the actuation of which an actual intensity value or an actual temporal intensity profile is determined for the image portion that shows the tissue segment at which the histology image forming the basis for the selected processed histological information item was recorded, and said actual intensity value or said actual temporal intensity profile is defined as a characteristic for the intensity or the temporal intensity profile of the at least one constituent part. A more objective selection can be made on the basis of the processed histological information item than on the basis of the histology image itself. Naturally, the selection can be made both on the basis of the histology image and on the basis of the processed histological information item. By way of example, the processed histological information item can be a value for the tumor cell proportion, a pH value, a value for the oxygen content, the concentration of $H_2O_2$ or other oxygen derivatives, etc.

In this variant, a treating physician or a treating team of physicians may for example record histology images until one has been found which shows a tissue segment that should be considered characteristic for the edge of the tumor or the edge of a certain region of the tumor, and then select the corresponding histology image. Following the selection, the actual intensity value for the image portion of the tissue field image showing this tissue segment, for example, is determined and defined as characteristic for the intensity of the at least one constituent part. The image regions of the tissue field image where the intensity corresponds to the characteristic can then be considered to be the edge of the tumor or the edge of a certain region of the tumor.

In a development of the first variant of the computer-implemented method according to the invention, the actual intensity value or the actual temporal intensity profile is determined in relation to each recorded histology image for the image portion of the tissue field image that corresponds to the tissue segment depicted in the histology image and the image regions in which the value of the intensity or the actual temporal intensity profile of the reflected or emitted light corresponds to the respectively determined actual intensity value or actual temporal intensity profile are marked in the tissue field image. This can indicate to the physician or the team of physicians how extensive the region of the tumor should be considered to be if the respective actual intensity value or the respective actual temporal intensity profile is used as a characteristic, and this may be of assistance for striking the balance in respect of removing as much tumor tissue as possible and at the same time preserving as much healthy tissue as possible. Then, one of the histology images can be selected on the basis of these considerations. The actual intensity value or the actual temporal intensity profile for the image portion of the tissue field image that corresponds to the tissue segment in the selected histology image can then be defined as a characteristic for the intensity or the temporal intensity profile of the at least one constituent part by actuating the selection function.

In a second variant of the method according to the invention, the at least one histological information item is a quantifiable histological information item, for instance a tumor cell proportion, and an actual value of the quantifiable histological information item which is determined on the basis of the histological information items and a specified value for the quantifiable histological information item which should mark the region of the tumor, for example the edge of the tumor, are used for determining the characteristic. By way of example, the tumor cell proportion may serve as quantifiable histological information item, with the tumor cell proportion being able to be considered, in a certain selected tissue segment, to be the proportion of tumor cells of the totality of all cells in this tissue segment. However, the quantifiable histological information item can also be, for example, the pH value, the oxygen content, the concentration of $H_2O_2$ or other oxygen derivatives, etc.

In particular, determining the actual value of the quantifiable histological information item can also be carried out within the scope of the computer-implemented method according to the invention itself, for example on the basis of a received histology image. Should the value of the quantifiable histological information item be the tumor cell proportion, the determination of the at least one actual tumor cell proportion may comprise the steps of:

- identifying tumor cells in the received histology image and
- determining the actual tumor cell proportion for the at least one received histology image on the basis of the number of identified tumor cells.

In this case, the histology image must facilitate the determination of the tumor cell proportion. By way of example, this may be an image obtained by means of a confocal endomicroscope, an image obtained by means of optical coherence tomography (OCT), an image obtained by means of a probe with a biosensor-type measurement function, an image obtained by means of magnetic resonance imaging (MRI), etc. However, it may also be a histological section image, that is to say an image of a histological section, or the like. By way of example, the histology image may have a resolution allowing the identification of individual cells in the image. Preferably, the resolution is even so high that the structures of individual cells, such as the cell nucleus, for example, can be identified. The resolution is preferably 10 μm or better, for example 5 μm, 3 μm, 1 μm, or 0.7 μm. By way of example, tumor cells can then be identified in the histology image on the basis of morphological criteria, for instance the cell structure, the size of the cell nucleus, etc., optionally with the aid of staining means for increasing the contrast. In this case, the histology image typically shows an object section of 1 $mm^2$ or less, for example 0.5 $mm^2$, 0.2 $mm^2$, 0.1 $mm^2$ or even less, whereas the tissue field image shows an object section of 1 $cm^2$ or more. If a dependence of the value of the intensity or of the temporal intensity profile of the at least one constituent part of the light reflected or emitted by the tissue is known, the intensity of the light reflected or emitted by the tissue can be used to determine the tumor cell proportion. This allows the value of the intensity or of the temporal intensity profile to be determined by means of the same apparatus that is also used to record the histology images.

Alternatively, the actual tumor cell proportion may also be determined externally and the determined actual tumor cell proportion forms an input into the method.

In this case, standard histological methods can be used to determine the tumor cell proportion. By way of example, a suitable method is described in Y. Jiang et al.: "*Calibration of fluorescence imaging for tumor surgical margin delineation: multistep registration of fluorescence and histological images*", Journal of Medical Imaging 6(2), 025005 (April to June 2019).

In a first embodiment of the second variant, the characteristic can be determined by:

- determining an actual intensity value or an actual temporal intensity profile of the intensity of the at least one constituent part for the image portion of the tissue field image that corresponds to the tissue segment for which the actual value of the quantifiable histological information item has been obtained,
- calculating a value for the intensity or the temporal intensity profile of the at least one constituent part at the specified value for the quantifiable histological information item on the basis of a dependence of the value of the intensity or of the temporal intensity profile of the at least one constituent part on the value of the quantifiable histological information item proceeding from the actual value of the quantifiable histological information item determined for the tissue segment of the tissue region and the actual intensity value determined for the image portion of the tissue field image or the actual temporal intensity profile determined for the image portion of the tissue field image corresponding to this tissue segment, and
- defining the calculated value for the intensity or the temporal intensity profile of the at least one constituent part at the specified value for the quantifiable histological information item as the characteristic for the intensity or the temporal intensity profile of the at least one constituent part.

In a second embodiment of the second variant, the characteristic can be determined by:

- receiving histology images and determining the actual value of the quantifiable histological information item for the tissue segments depicted in the received histology images until a tissue segment has been found for which the actual value of the quantifiable histological information item corresponds to the specified value for the quantifiable histological information item, the tissue segments being located in the tissue region depicted in the tissue field image;
- selecting the image portion that represents the tissue segment in which the actual value of the quantifiable histological information item corresponds to the specified value for the quantifiable histological information item;
- determining the actual intensity value or the actual temporal intensity profile of the intensity of the at least one constituent part for the selected image portion; and
- defining the actual intensity value or the actual temporal intensity profile of the selected image portion as the characteristic for the intensity or the temporal intensity profile of the at least one constituent part.

Since not only the determination of the actual value of the quantifiable histological information item but also the remaining steps can be implemented in automated fashion in the second variant, the determination of the characteristic on the basis of a recorded histology image or a plurality of recorded histology images can be implemented in automated fashion in this variant.

Thus, in the second variant of the computer-implemented method according to the invention, histological information items, which in particular may be available in the form of histology images, are used to determine the tumor cell proportion, for example, for a certain tissue segment of the tissue region depicted in the tissue field image. Moreover, the intensity or the temporal intensity profile of the at least one constituent part is measured for the image segment of the tissue field image that represents the tissue segment for which the tumor cell proportion has been determined. The intensity or the temporal intensity profile of the constituent part that can be expected in the case of the specified tumor cell proportion can then be calculated from a dependence of the intensity or of the temporal intensity profile of the at least one constituent part on the tumor cell proportion. Should such a calculation be undesirable or impossible, for example because no such dependence of the intensity or of the temporal intensity profile on the tumor cell proportion is known, there alternatively is the option of determining actual tumor cell proportions for tissue segments of the tissue region until a tissue segment whose actual tumor cell proportion corresponds to the specifying tumor cell proportion has been found. For the image portion depicting this tissue segment in the tissue field image, the actual intensity value or the actual temporal intensity profile of the at least one constituent part then is determined. However, calculating the intensity or the temporal intensity profile of the constituent part that is to be expected for the specified tumor cell proportion in this case offers the advantage that histological information items only have to be obtained once and only a single actual tumor cell proportion needs to be determined. This applies not only to the tumor cell proportion but also to other quantifiable histological information items such as, for example, the pH value, the oxygen content, the concentration of $H_2O_2$ or other oxygen derivatives, etc.

The tissue field image in the computer-implemented method according to the invention can be a fluorescence image, in particular. In this case, the intensity or the temporal intensity profile of the at least one constituent part is the intensity or the temporal intensity profile of at least one spectral line of the fluorescence radiation emitted by the tissue region. Methods where fluorescing dyes are used to identify tumors are widespread and facilitate a particularly good distinction between tumor cells and healthy cells. Accordingly, the intensity or the temporal intensity profile of the fluorescence radiation is a good measure for the proportion of tumor cells in a tissue segment, for example.

In order to be able to reduce falsifications as a result of ambient conditions when the intensity or the temporal intensity profile of the at least one constituent part is determined, the computer-implemented method according to the invention can be embodied in such a way that the value of the actual intensity or of the temporal intensity profile of the at least one constituent part is corrected on the basis of at least one of the data records contained in the following group:

- A data record representing the reflection properties of the tissue region, with the aid of which specular reflections of the tissue region, for example, can be corrected.
- A data record representing the topography of the tissue region, with the aid of which it is possible to take into account different reflection or emission directions that are caused by the topography.
- A data record representing at least one equipment parameter of the recording apparatus used to record the tissue field image, by means of which it is possible to consider, for example, the set illumination intensity, the illumination spectrum, intensity losses due to inserted filters, etc.

Moreover, the invention provides a method for producing a processed tissue field image of a tissue region with a tumor, in which a region of the tumor is marked. The method comprises the steps of:

- obtaining at least one histological information item for at least one tissue segment of the tissue region. The at least one histological information item may be contained in particular in a histology image recorded at the image portion of the tissue field image. By way of example, the histology image can be recorded by means of an endomicroscope, for example by means of a confocal endomicroscope or an endomicroscope suitable for carrying out optical coherence tomography.
- recording a tissue field image of the tissue region. In this case, the tissue field image typically is a large-area image which represents an object field with an area of 1 $cm^2$ or more, for example 2 $cm^2$, 5 $cm^2$ or even more. In particular, this may be an image obtained by a surgical microscope, that is to say it may be recorded with a magnification as well. However, the magnification is not so high in this case as to render cellular structures identifiable. Typically, the magnification is in the range from approximately 5× to approximately 40×.
- carrying out the computer-implemented method according to the invention on the basis of the at least one obtained histological information item and the recorded tissue field image, the tissue field image with the marked region of the tumor forming the processed tissue field image.

By way of example, the method according to the invention can be used to process an image recorded by a surgical microscope in order to indicate to a treating surgeon the boundaries of a tumor if the region of the tumor represents the entire tumor or the boundaries of a certain region of the tumor, for example the boundaries of the region of the tumor in which a tumor-specific property, for instance the pH value, the oxygen content, the concentration of $H_2O_2$ or other oxygen derivatives, etc., is above or below a certain limit.

In this case, the coordinates of the tissue segment from which the at least one histological information item was obtained can be stored, and a recording apparatus used to record the tissue field image can be aligned by means of a navigation system so that the tissue segment from which the at least one histological information item was obtained is imaged in an image portion of the tissue field image. In this way, it is possible to ensure that an image portion showing the tissue segment is available in the tissue field image for the tissue segment from which the at least one histological information item was obtained.

Moreover, the method may comprise specifying a value for a quantifiable histological information item, for example a value for the tumor cell proportion intended to mark the edge of the region of the tumor, and determining or receiving an actual value of the quantifiable histological information item, for example an actual tumor cell proportion, for at least one tissue segment of the tissue region depicted in an image portion of the tissue field image. To determine the actual value of the quantifiable histological information item, a histology image containing the quantifiable histological information item, on the basis of which the actual value of the quantifiable histological information item is determined, can be recorded for at least one tissue segment depicted in an image portion of the tissue field image. If an actual value of the quantifiable histological information item is received, the latter is determined externally on the basis of the histological information items.

In particular, a fluorescence image can be recorded as the tissue field image, with the intensity or the temporal intensity profile of the at least one constituent part then being the intensity or the temporal intensity profile of at least one spectral line of the fluorescence radiation emitted by the tissue region.

The surgical microscope may comprise a hyperspectral sensor or a multispectral sensor for the purposes of recording the tissue field image. In addition or as an alternative thereto, the endomicroscope may comprise a hyperspectral sensor or a multispectral sensor for the purposes of recording the histology image. While a conventional image sensor can only differentiate between three primary colors, a multispectral sensor offers the possibility of differentiating between more than three primary colors and a hyperspectral sensor offers the possibility of differentiating between a multiplicity of colors. As a result, detecting the intensity or the temporal intensity profile of the at least one constituent part particularly precisely is rendered possible.

Moreover, according to the invention, a computer program is provided for marking a region of a tumor in a tissue field image which shows a tissue region with a tumor and which has been obtained by means of light reflected or emitted by the tissue region. The computer program comprises instructions which, when executed on a computer, prompt the computer to mark the region of the tumor on the basis of a characteristic for the intensity or for the temporal intensity profile of at least one constituent part of the light reflected or emitted by the tissue region. According to the invention, the computer program comprises instructions which prompt the computer to determine the characteristic on the basis of the intensity or the temporal intensity profile of the at least one constituent part in an image portion of the tissue field image that corresponds to a tissue segment of the tissue region from which at least one histological information item was obtained.

The computer program according to the invention facilitates the performance of the computer-implemented method according to the invention on a computer or any other data processing system. In this case, the computer program can be developed in such a way that it facilitates the performance of the developments of the computer-implemented method on a computer or any other data processing system.

Furthermore, the present invention provides a non-volatile computer-readable storage medium with instructions stored thereon for marking a region of a tumor in a tissue field image which shows a tissue region with a tumor and which has been obtained by means of light reflected or emitted by the tissue region. The instructions stored on the storage medium comprise instructions which, when executed on a computer, prompt the computer to mark the region of the tumor on the basis of a characteristic for the intensity or for the temporal intensity profile of at least one constituent part of the light reflected or emitted by the tissue region. The stored instructions moreover comprise instructions which prompt the computer to determine the characteristic on the basis of the intensity or the temporal intensity profile of the at least one constituent part in an image portion of the tissue field image that corresponds to a tissue segment of the tissue region from which at least one histological information item was obtained.

The non-volatile computer-readable storage medium according to the invention allows the computer program according to the invention to be loaded onto a computer or any other data processing system and hence allows the computer or the data processing system to be configured for carrying out the computer-implemented method according to the invention. In this case, the instructions stored on the non-volatile computer-readable storage medium may also comprise instructions that facilitate the performance of the developments of the computer-implemented method according to the invention.

According to a further aspect of the present invention, a data processing system having a processor and at least one memory is provided, with the processor being designed to mark, on the basis of instructions of a computer program stored in the memory, a region of a tumor in a tissue field image which shows a tissue region with a tumor and which has been obtained by means of light reflected or emitted by the tissue region, and to mark the region of the tumor on the basis of a characteristic for the intensity or for the temporal intensity profile of at least one constituent part of the light that was reflected or emitted by the tissue region. In the data processing system according to the invention, the computer program stored in the memory comprises instructions which prompt the processor to determine the characteristic on the basis of the intensity or the temporal intensity profile of the at least one constituent part in an image portion of the tissue field image that corresponds to a tissue segment of the tissue region from which at least one histological information item was obtained.

The data processing system according to the invention, which may be in the form of a computer or any other data processing device, facilitates the performance of the computer-implemented method according to the invention. In this case, the data processing system can be developed in such a way that the instructions stored in the memory facilitate the performance of the developments of the computer-implemented method according to the invention.

Moreover, according to the invention, a medical apparatus is provided for producing a processed tissue field image of a tissue region with a tumor, in which a region of the tumor is marked. The medical apparatus according to the invention comprises an image recording apparatus for recording a tissue field image of a tissue region with a tumor. The image recording apparatus can be a camera or an image sensor integrated into different equipment. By way of example, the image recording apparatus may be an image sensor integrated into a surgical microscope. Moreover, the medical apparatus comprises an interface for receiving at least one histological information item, which has been obtained for a tissue segment of the tissue region depicted in an image portion of the tissue field image, and/or for receiving a histology image, on the basis of which the at least one histological information item can be obtained. Alternatively, the medical apparatus may also comprise a histology image recording apparatus for recording such a histology image, for instance an endomicroscope. Moreover, the medical apparatus comprises a data processing system according to the invention. Hence, the medical apparatus according to the invention can carry out the computer-implemented method according to the invention and optionally the developments thereof. By way of example, the histological information item can in this case be a tumor cell proportion, the oxygen content of the tumor cells, a variable derived from the morphology of the tumor cells, etc.

As an image sensor, the image recording apparatus of the medical apparatus may comprise a hyperspectral sensor or a multispectral sensor. In addition or as an alternative thereto, the histology image recording apparatus may comprise a hyperspectral sensor or a multispectral sensor. This renders it possible to particularly exactly determine the intensity or the temporal intensity profile of certain wavelengths.

Furthermore, the medical apparatus may comprise an input device for specifying a value for a quantifiable histological information item that is intended to characterize the edge of the region of the tumor. By way of example, this input device can be a keyboard or a touchscreen. However, it may also be a voice recognition system, by means of which a value for the quantifiable histological information item, for example, can be entered by speech, or a data interface, by means of which a specified value for the quantifiable histological information item, for example, can be transmitted to the medical apparatus.

A light source comprising a spectral characteristic that is able to induce fluorescence in the tissue region can be used as a light source. In particular, the spectral characteristic can be realized in this case by an emitter whose spectral maximum is located in the infrared spectral range or in the ultraviolet spectral range. However, it may also be realized by a broadband emitter in conjunction with a spectral filter.

Further features, properties and advantages of the present invention will become apparent from the following description of exemplary embodiments with reference to the accompanying figures.

Figure 5:
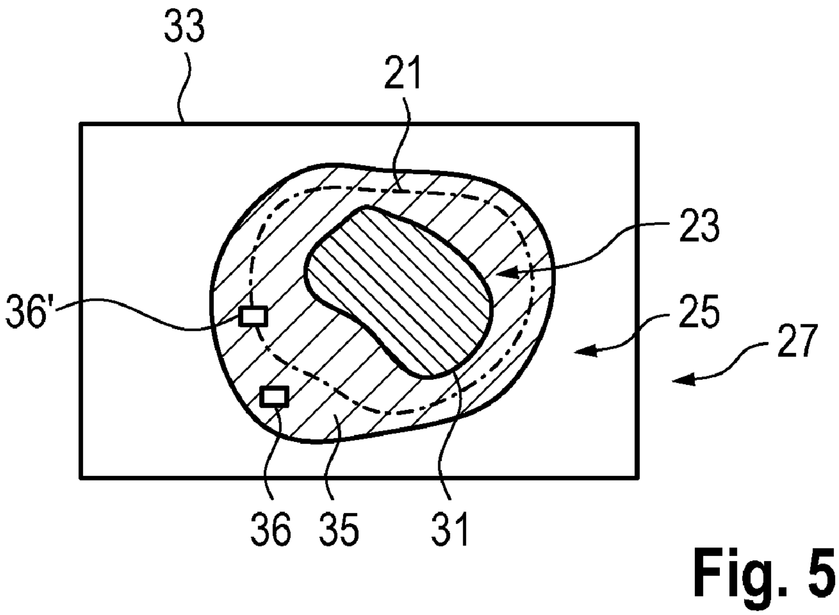

FIG. 5 very schematically shows a tissue field image exhibiting a tumor, in which the edge of the tumor has been emphasized.

Figure 6:
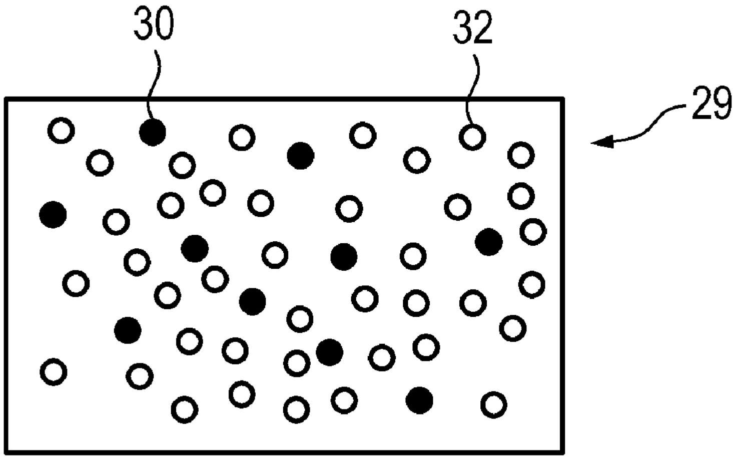

FIG. 6 very schematically shows a histology image which can be used to determine an actual tumor cell proportion.

Figure 7:
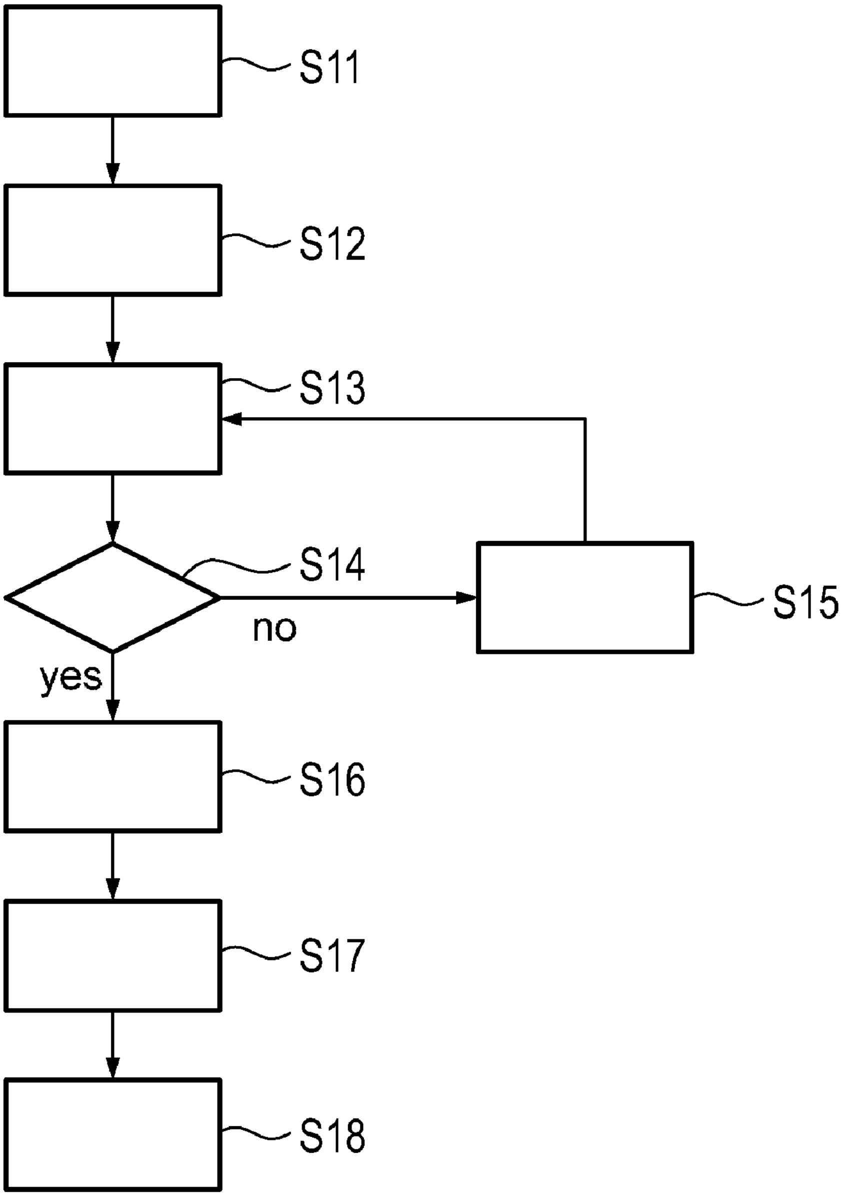

FIG. 7 shows a flowchart of a second exemplary embodiment of a method for marking the edge of a tumor in a tissue field image.

Figure 8:
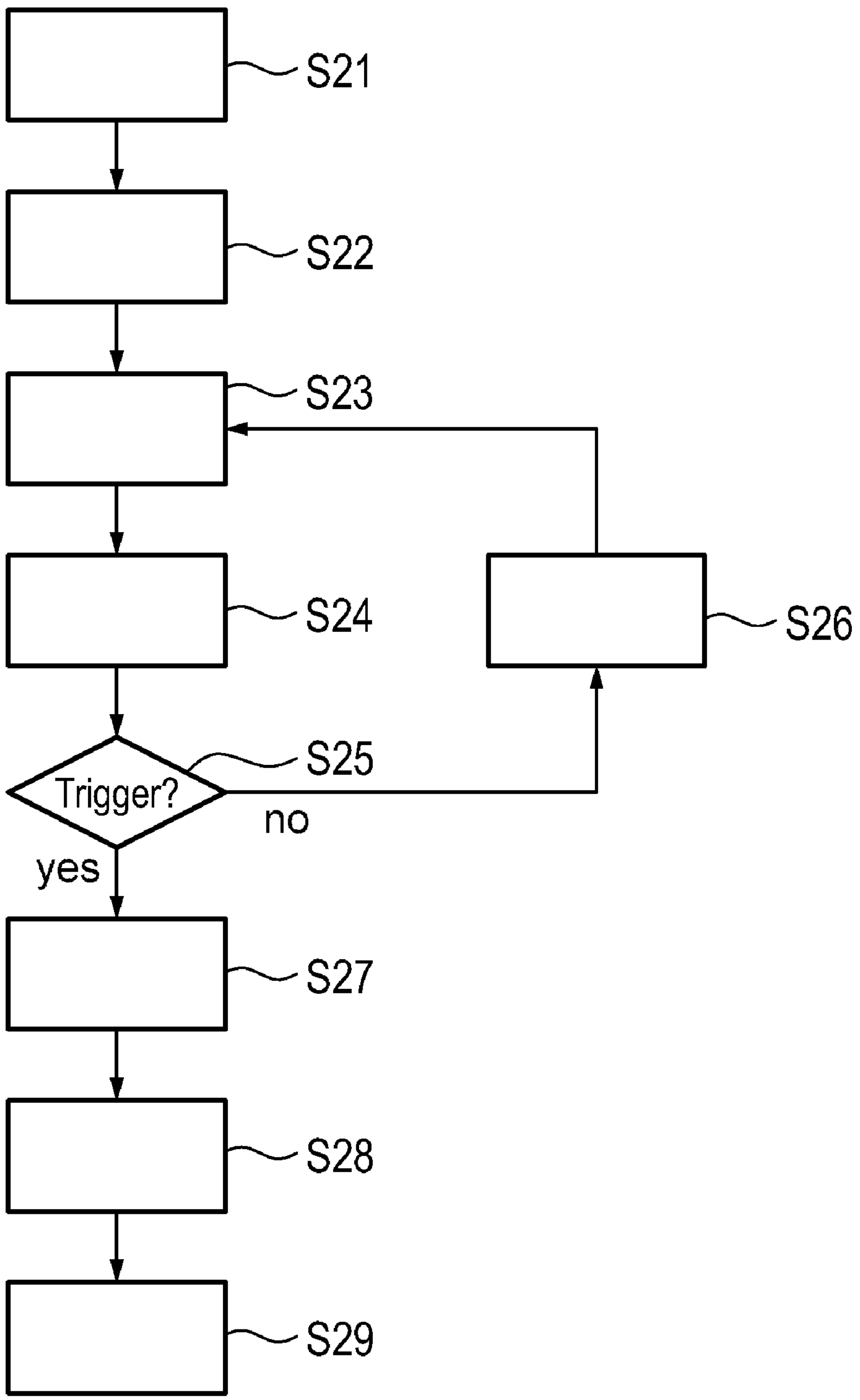

FIG. 8 shows a flowchart of a third exemplary embodiment of a method for marking the edge of a tumor in a tissue field image.

Figure 1:
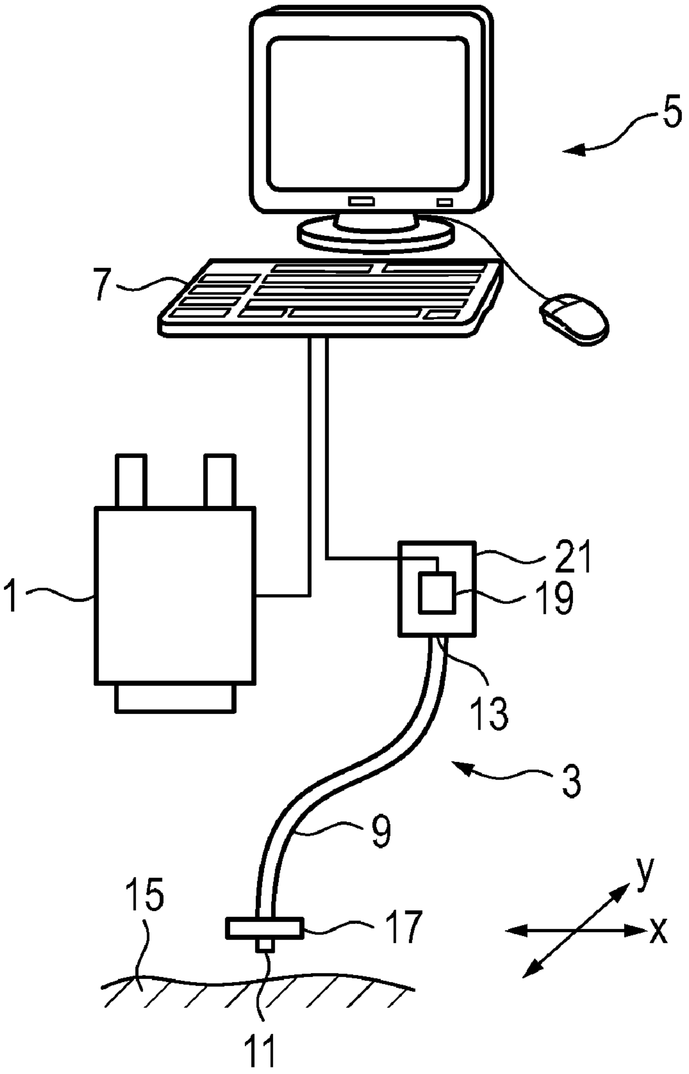
FIG. 1 shows a schematic representation of a medical apparatus for producing a processed tissue field image of a tissue region with a tumor, in which the edge of the tumor is emphasized.

For explanatory purposes, the invention will be described in detail below on the basis of exemplary embodiments. As an exemplary embodiment for a medical apparatus for producing a processed tissue field image of a tissue region with a tumor, in which the edge of the tumor is emphasized, FIG. 1 shows a system comprising a surgical microscope 1 as an image recording apparatus, an endomicroscope 3 as a histology image recording apparatus, and a computer 5 as a data processing system. In this case, the keyboard 7 of the computer 5 can serve as an input device for specifying a value for a quantifiable histological information item, for example for specifying a tumor cell proportion.

The endomicroscope 3 shown in FIG. 1 comprises an optical fiber 9 with a first end 11 and a second end 13. The first end 11 is made to face the observation object 15, which is a tissue region 25 with a tumor 23 in the present exemplary embodiment (see FIG. 5), and is located in a scanning device 17, with the aid of which the first end 11 can be moved along two lateral directions, referred to as x-direction and y-direction below, with respect to the observation object 15. In particular, the scanning device can be realized by means of microelectromechanical systems (MEMS). By way of example, a scanning device using microelectromechanical systems is described in US 2016/0051131 A1. Reference is made to this document in respect of the structure of a suitable scanning device.

The second end 13 of the optical fiber 9 faces a sensor 19, by means of which it is possible to capture luminous energy incident on the sensor 19. The sensor 19 is located in a housing 21, which is embodied as a separate module in the present exemplary embodiment but which can also be embodied as a handle, and in which, moreover, a light source (not illustrated in the figure) for generating illumination light for illuminating the observation object 15 and an input coupling apparatus for coupling the illumination light into the second end 13 of the optical fiber 9 are housed. In particular, the light source can be a laser light source. However, the light source can also be arranged outside of the housing 21 and be connected to the latter by way of a light guide. Then, the output end of the light guide is situated in the housing 21. In this case, the input coupling apparatus input couples the illumination light of the optical fiber 9 emerging from the output end of the light guide. The illumination light can be white light, i.e., have a broadband spectrum, or light with a spectrum that consists of one or more narrowband spectral ranges, in particular spectral lines, for example of one or more narrowband spectral ranges or spectral lines suitable for exciting a fluorescence of a fluorescent dye situated in the observation object 15. By way of example, the fluorescent metabolite protoporphyrin IX (PpIX) is a suitable fluorescent dye.

Illumination light coupled into the second end 13 of the optical fiber 9 is guided through the optical fiber 9 to the first end 11, from where the illumination light emerges in the direction of the observation object 15. Illumination light reflected by the observation object 15 or light excited by the illumination light and emitted by the observation object 15, for instance fluorescent light, enters into the first end 11 of the optical fiber 9 in turn and is guided from the latter to the second end 13, from where it emerges in the direction of the sensor 19. Moreover, focusing optical units can be located at, or in front of, the ends 11, 13 of the optical fiber 9 and these can be used to focus light onto the surface of the observation object 15 or onto the sensor 19. In particular, the endomicroscope 3 can be embodied as a confocal endomicroscope. In addition or as an alternative thereto, it can also be embodied as an endomicroscope for carrying out optical coherence tomography (OCT). Confocal microscopy and optical coherence tomography are well-known methods and are described in US 2010/0157308 A1 and U.S. Pat. No. 9,921,406 B2, for example. Therefore, the description of details in respect of confocal microscopy and in respect of optical coherence tomography is dispensed with in the scope of the present description. Instead, reference is made to US 2010/0157308 A1 and U.S. Pat. No. 9,921,406 B2.

Recording the image with the aid of the endomicroscope 1 is controlled with the aid of the computer 5 in the present exemplary embodiment. However, the control can also be implemented by means of a dedicated control device. The computer 5 used for controlling in the present exemplary embodiment is connected both to the scanning device 17 and to the sensor 19. In the present exemplary embodiment, the scanning device 17 is controlled by the computer 5 in such a way that the observation object 15 is scanned along a grid with grid points. At each scanned grid point there is an illumination of the observation object 15 with illumination light and a recording of the reflected illumination light or of the light emitted by the observation object 15 on account of an excitation by means of the illumination light. Then, the computer generates an image from the reflected illumination light recorded at the grid points or from the light emitted by the observation object recorded at the grid points, the pixel grid of said image corresponding to the grid used during the scanning. The resolution of the image produced thus is typically 10 μm or better, for example 5 μm, 3 μm, 1 μm, 0.7 μm, or even better. In this case, the image typically shows an object section of 1 $mm^2$ or less, for example 0.5 $mm^2$, 0.2 $mm^2$, 0.1 $mm^2$ or even less. In the present exemplary embodiment, the optical fiber 9, the scanning device 17, the sensor 19, and the computer 5 together form a histology image recording apparatus, that is to say a recording apparatus for recording an image that facilitates the determination of histological information items, in particular quantifiable histological information items such as, for instance, the tumor cell proportion of the tissue depicted in the image or the oxygen content, the pH value, the concentration of $H_2O_2$ or other oxygen derivatives, etc., of the tissue depicted in the image. By way of example, tumor cells can then be identified in the histology image on the basis of morphological criteria, for instance the cell structure, the size of the cell nucleus, etc., optionally with the aid of staining means for increasing the contrast.

Figure 2:
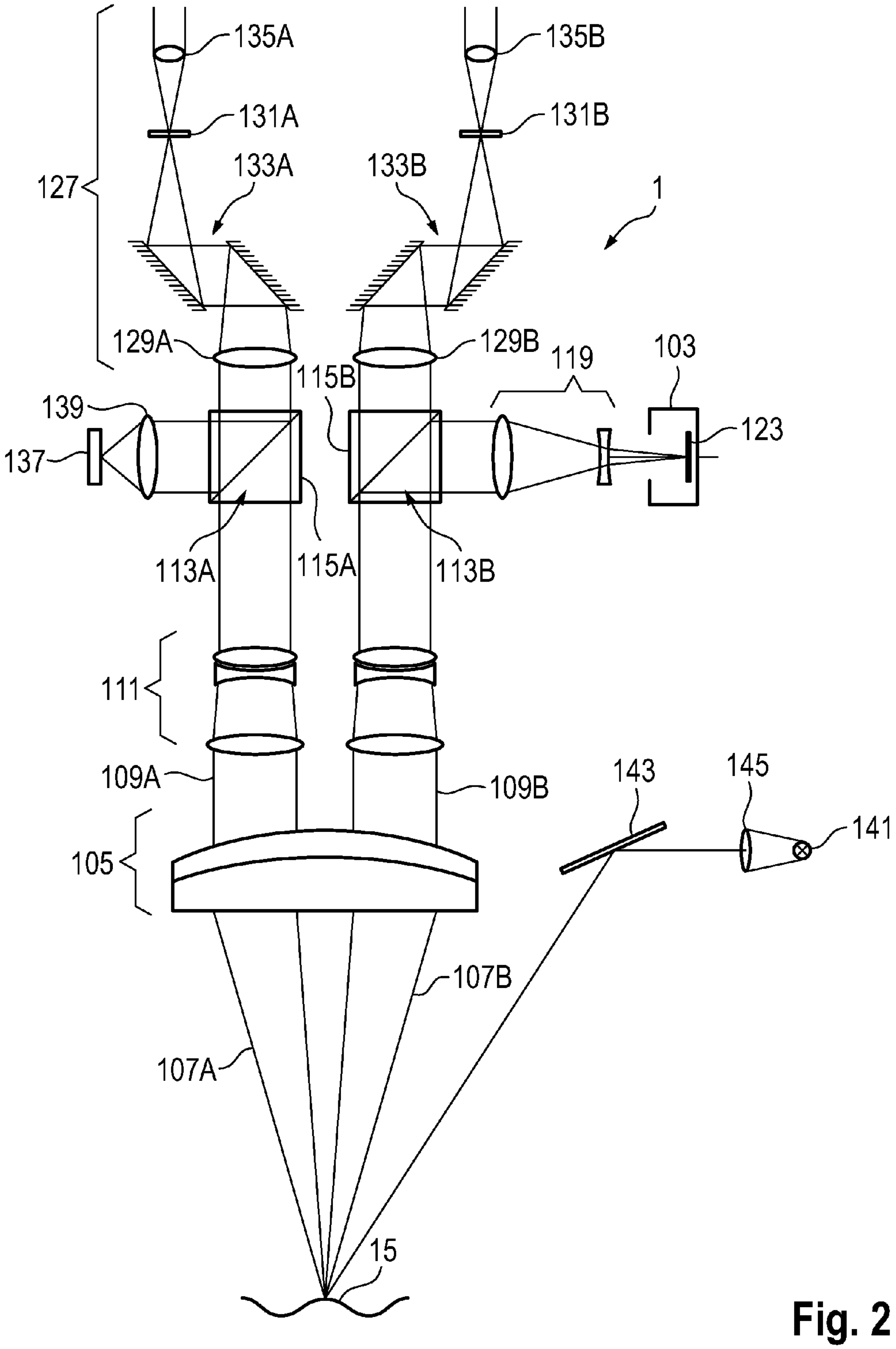
FIG. 2 shows the structure of a surgical microscope in a schematic illustration.
Figure 3:
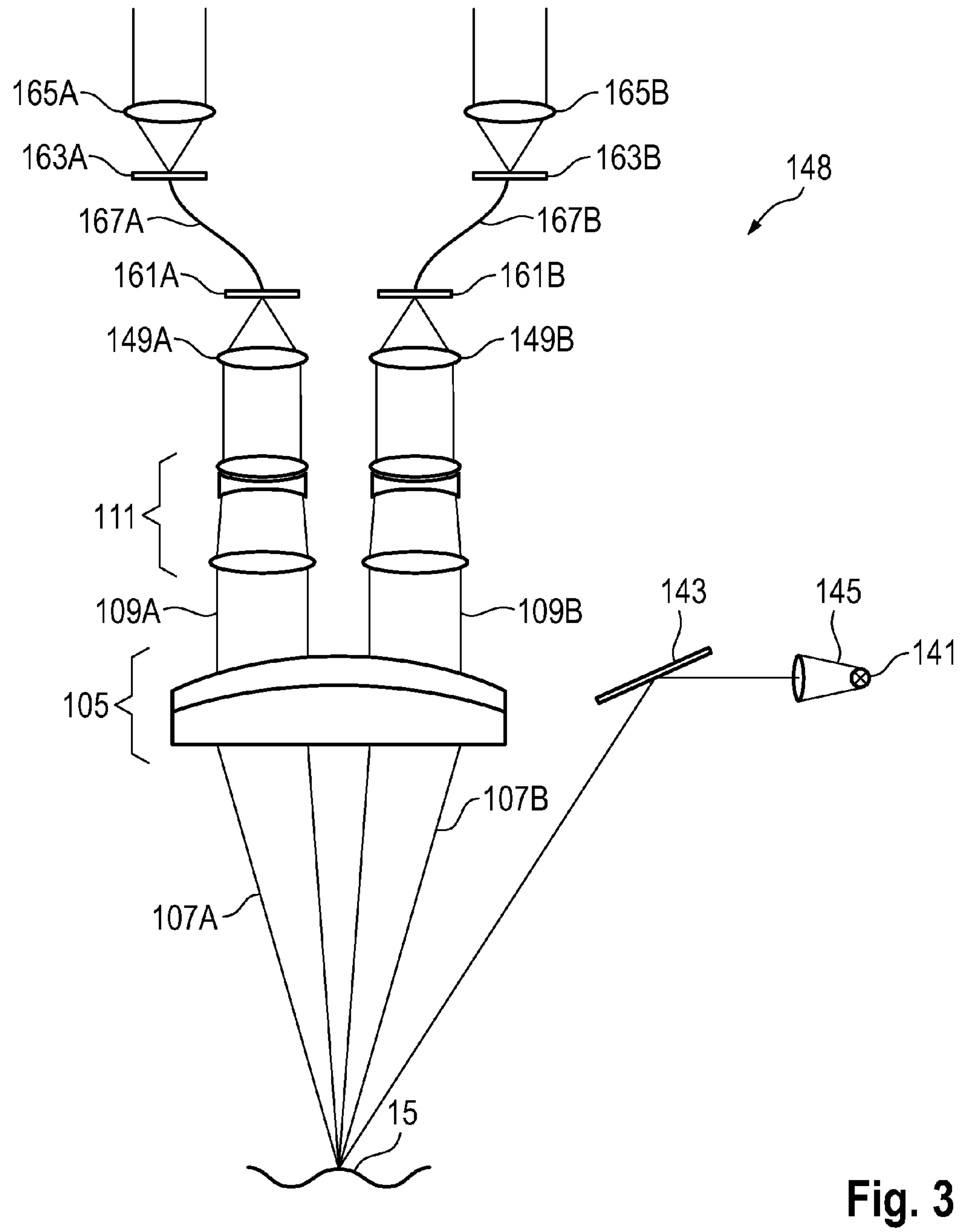
FIG. 3 shows an alternative embodiment of the surgical microscope.

FIG. 2 shows a schematic illustration of a possible structure of the surgical microscope 1, as can find use in the arrangement of FIG. 1. FIG. 3 shows a possible alternative structure.

The surgical microscope 1 shown in FIG. 2 comprises, as essential components, an objective 105 that is to face an observation object 15, that is to say the tissue region with a tumor in the present exemplary embodiment, which objective can be embodied in particular as an achromatic or apochromatic objective. In the present exemplary embodiment, the objective 105 consists of two partial lenses that are cemented to one another and form an achromatic objective. The observation object 15 is arranged in the focal plane of the objective 105 such that it is imaged at infinity by the objective 105. Expressed differently, a divergent beam 107A, 107B emanating from the observation object 15 is converted into a parallel beam 109A, 109B during its passage through the objective 105.

A magnification changer 111 is arranged on the observer side of the objective 105, which magnification changer can be embodied either as a zoom system for changing the magnification factor in a continuously variable manner as in the illustrated embodiment, or as what is known as a Galilean changer for changing the magnification factor in a stepwise manner. In a zoom system, constructed by way of example from a lens combination having three lenses, the two object-side lenses can be displaced in order to vary the magnification factor. In actual fact, however, the zoom system also can have more than three lenses, for example four or more lenses, in which case the outer lenses then can also be arranged in a fixed manner. In a Galilean changer, by contrast, there are a plurality of fixed lens combinations which represent different magnification factors and which can be introduced into the beam path alternately. Both a zoom system and a Galilean changer convert an object-side parallel beam into an observer-side parallel beam having a different beam diameter. In the present exemplary embodiment, the magnification changer 111 is already part of the binocular beam path of the surgical microscope 1, i.e., it has a dedicated lens combination for each stereoscopic partial beam path 109A, 109B of the surgical microscope 1. In the present exemplary embodiment, a magnification factor is adjusted by means of the magnification changer 111 by way of a motor-driven actuator which, together with the magnification changer 111, is part of a magnification changing unit for adjusting the magnification factor.

The magnification changer 111 is adjoined on the observer side by an interface arrangement 113A, 113B, by means of which external devices can be connected to the surgical microscope 1 and which comprises beam splitter prisms 115A, 115B in the present exemplary embodiment. However, in principle, use can also be made of other types of beam splitters, for example partly transmissive mirrors. In the present exemplary embodiment, the interfaces 113A, 113B serve to output couple a beam from the beam path of the surgical microscope 1 (beam splitter prism 115B) and to input couple a beam into the beam path of the surgical microscope 1 (beam splitter prism 115A).

In the present exemplary embodiment, the beam splitter prism 115A in the partial beam path 109A serves to mirror information or data for an observer into the partial beam path 109A of the surgical microscope 1 with the aid of a display 137, for example a digital mirror device (DMD) or an LCD display, and an associated optical unit 139 by means of the beam splitter prism 115A. By way of example, a marking line that marks the course of the edge of the tumor in the observed tissue region can be overlaid on the image obtained by the surgical microscope 1. A camera adapter 119 with a camera 103 secured thereto, said camera being equipped with an electronic image sensor 123, for example with a CCD sensor or a CMOS sensor, is arranged at the interface 113B in the other partial beam path 109B. It is possible by means of the camera 103 to record an electronic image and, in particular, a digital image of the observation object 15. The image sensor used can also be, in particular, a multispectral sensor or a hyperspectral sensor comprising not just three spectral channels (e.g., red, green, and blue), but rather a multiplicity of spectral channels.

The interface 113 is followed on the observer side by a binocular tube 127. The latter has two tube objectives 129A, 129B, which focus the respective parallel beam 109A, 109B onto an intermediate image plane 131, i.e., image the observation object 15 onto the respective intermediate image plane 131A, 131B. The intermediate images situated in the intermediate image planes 131A, 131B are finally imaged at infinity in turn by eyepiece lenses 135A, 135B, such that an observer can observe the intermediate image with a relaxed eye. Moreover, the distance between the two partial beams 109A, 109B is increased in the binocular tube by means of a mirror system or by means of prisms 133A, 133B in order to adapt said distance to the interocular distance of the observer. In addition, image erection is carried out by the mirror system or the prisms 133A, 133B.

The surgical microscope 1 moreover is equipped with an illumination apparatus, by means of which the observation object 15 can be illuminated with illumination light. To this end, the illumination apparatus in the present exemplary embodiment has a white-light source 141, for example a halogen lamp or a gas discharge lamp. The light emanating from the white-light source 141 is directed in the direction of the observation object 15 via a deflection mirror 143 or a deflection prism in order to illuminate said field. Furthermore, an illumination optical unit 145 is present in the illumination apparatus, said illumination optical unit ensuring uniform illumination of the entire observed observation object 15.

The illumination can be influenced in the surgical microscope 1 illustrated in FIG. 2. By way of example, a filter can be introduced into the illuminating beam path, said filter transmitting only a narrow spectral range from the wide spectrum of the white-light source 141, e.g., a spectral range that enables the excitation of fluorescence of a fluorescent dye situated in the observation object 15. In order to observe the fluorescence, filters 137A, 137B can be introduced into the observation partial beam paths, said filters filtering out the spectral range used to excite the fluorescence so that said fluorescence can be observed. To illuminate the observation object 15 only using the spectral range of the illumination light required for exciting the fluorescence, there is the option of using a narrowband light source, for example a laser light source, which substantially only emits in the spectral range required for exciting the fluorescence, rather than using a white-light source in conjunction with a filter. In particular, the illumination apparatus may also comprise a device facilitating an interchange between a white-light source and a narrowband light source.

It should be pointed out the illumination beam path illustrated in FIG. 2 is highly schematic and does not necessarily reproduce the actual course of the illumination beam path. In principle, the illumination beam path can be designed as what is known as oblique illumination, which comes closest to the schematic illustration in FIG. 2. In such oblique illumination, the beam path extends at a relatively large angle (6° or more) with respect to the optical axis of the objective 5 and, as illustrated in FIG. 2, may extend completely outside the objective. Alternatively, however, there is also the possibility of allowing the illumination beam path of the oblique illumination to extend through a marginal region of the objective 105. A further possibility for the arrangement of the illumination beam path is what is known as 0° illumination, in which the illumination beam path extends through the objective 105 and is input coupled into the objective 105 between the two partial beam paths 109A, 109B, along the optical axis of the objective 105 in the direction of the observation object 15. Finally, it is also possible to design the illumination beam path as what is known as coaxial illumination, in which a first illumination partial beam path and a second illumination partial beam path are present. The partial beam paths are coupled into the surgical microscope 1 via one or more beam splitters parallel to the optical axes of the observation partial beam paths 109A, 109B, such that the illumination extends coaxially with respect to the two observation partial beam paths.

In the embodiment variant of the surgical microscope 1 shown in FIG. 2, the objective 105 consists only of one achromatic lens. However, use can also be made of an objective lens system made of a plurality of lenses, in particular a so-called vario-objective, by means of which it is possible to vary the working distance of the surgical microscope 1, i.e., the distance between the object-side focal plane and the vertex of the first object-side lens surface of the objective 105, also referred to as front focal distance. The observation object 15 arranged in the focal plane is imaged at infinity by a vario-objective, too, and so a parallel beam is present on the observer side.

FIG. 3 shows one example of a digital surgical microscope 148 in a schematic representation. In this surgical microscope, the main objective 105, the magnification changer 111, and the illumination system 141, 143, 145 do not differ from the surgical microscope 1 with the optical viewing unit that is illustrated in FIG. 2. The difference lies in the fact that the surgical microscope 148 shown in FIG. 3 does not comprise an optical binocular tube. Instead of the tube objectives 129A, 129B from FIG. 2, the surgical microscope 148 from FIG. 3 comprises focusing lenses 149A, 149B, by means of which the binocular observation beam paths 109A, 109B are imaged on digital image sensors 161A, 161B. Here, the digital image sensors 161A, 161B can be, for example, CCD sensors or CMOS sensors. The images recorded by the image sensors 161A, 161B are transmitted to digital displays 163A, 163B, which may be embodied as LED displays, as LCD displays, or as displays based on organic light-emitting diodes (OLEDs). As in the present example, eyepiece lenses 165A, 165B can be assigned to the displays 163A, 163B, by means of which lenses the images presented on the displays 163A, 163B are imaged at infinity such that a viewer can view said images with relaxed eyes. The displays 163A, 163B and the eyepiece lenses 165A, 165B can be part of a digital binocular tube; however, they can also be part of a head mounted display (HMD) such as, e.g., a pair of smartglasses. Naturally, the images recorded by the image sensors 161A, 161B can also be transferred to a monitor. Suitable shutter glasses can be used for the three-dimensional observation of the image depicted on the monitor.

Figure 4:
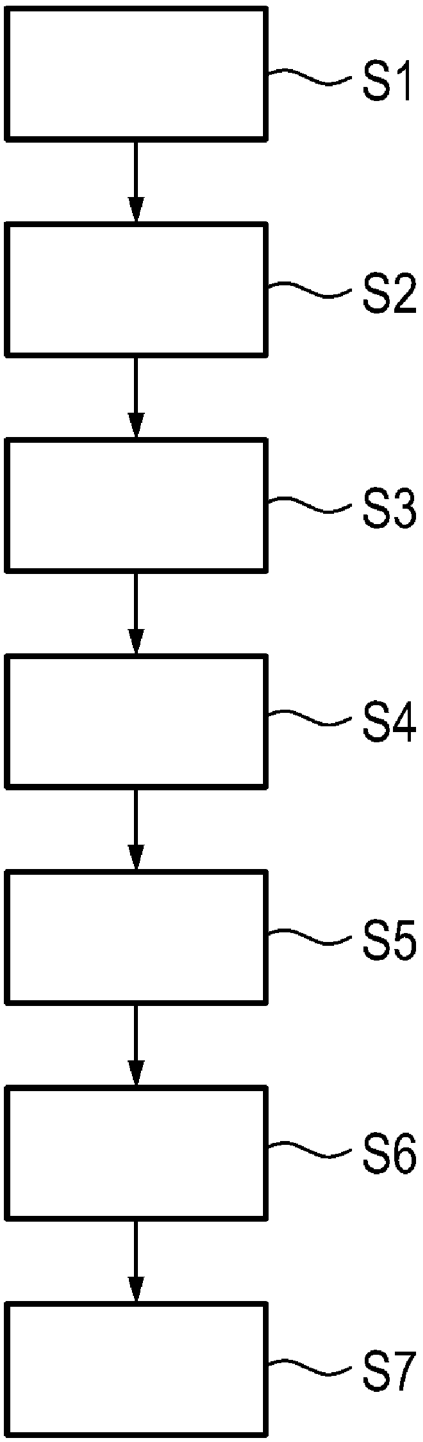
FIG. 4 shows a flowchart of a first exemplary embodiment of a method for marking the edge of a tumor in a tissue field image.

A first exemplary embodiment of a method for producing a processed tissue field image 27, which shows a tissue field 25 with a tumor 23, is described below with reference to FIGS. 4 to 6. In this case, FIG. 4 shows a flowchart which represents the method steps implemented on the computer 5. FIG. 5 shows a schematic representation of the processed tissue field image 27 and FIG. 6 shows a schematic representation of a histology image 29, as is used within the scope of producing the processed tissue field image 27.

In the processed tissue field image 27 of the present exemplary embodiment, the edge of the tumor 23 is marked by a marking line 21 that encloses a region of the tissue region 25 which is depicted in the tissue field image 27 and in which the tumor cell proportion has or exceeds a specified value. Consequently, the marking line 21 can be considered to be a line that represents the edge of the tumor. Alternatively, the method can also be designed in such a way that the edge delimits a certain region of the tumor, for example a region in which the oxygen content of the tumor cells does not exceed a certain value.

The recording of the tissue field image 27, which is processed with the aid of the method described below, is implemented by means of the surgical microscope 1, that is to say by means of at least one image sensor contained in the surgical microscope 1. The at least one histology image 29 is recorded with the aid of the endomicroscope 3. Then, the tissue field image 27 is processed for the purposes of marking the edge of the tumor 23 on the basis of the not yet processed tissue field image 27 and the at least one histology image. The tissue field image 27 is a large-area image which shows at least 1 $cm^2$, preferably at least 2 $cm^2$, and typically 5 $cm^2$, or more, of the observation object. In the present exemplary embodiment, this is recorded using a fluorescent dye that accumulates in the tumor cells but not in healthy tissue cells. To render the fluorescence visible, the observation object is illuminated with light having a tight spectrum suitable for exciting the fluorescence. Then, filters that block the excitation radiation are introduced into the observation beam path of the surgical microscope 1 so that only the fluorescence radiation can pass the observation beam path, and not reflected excitation light. Within the scope of a method known as Blue 400™ by Carl Zeiss Meditec AG, protoporphyrin IX (abbreviated PpIX) is used as the dye and leads to the tumor 23 being represented in the tissue field image 27 by a red fluorescent region 31 against a blue background 33. On account of the infiltrating character of the tumor cells, for example in the case of glioblastoma, there is a transition region 35 in which both tumor cells and healthy tissue cells are present, and this leads to this region having a hue that represents a mixed color between red and blue, the hue being redder with an increasing proportion of tumor cells in the cells of a tissue segment.

When removing a tumor, the treating surgeon has the difficulty of on the one hand wishing to remove as much tumor tissue as possible to increase the patient's prospects of a cure but on the other hand wishing to spare healthy tissue, especially healthy brain tissue in the case of brain tumors. It is therefore common practice to locate the edge of the tumor in the transition region 35, for example at locations where the fluorescence has a certain intensity value. However, since a variation in the fluorescence of tumor cells of a certain tumor type between different patients and between different tumors cannot be excluded, this type of defining the edge of the tumor is afflicted by fuzziness. The same difficulty also occurs in other fluorescent dyes to the ones used in the Blue 400™ method. Using the methods described in the present exemplary embodiment it is possible to determine an individual intensity value for a patient, which marks the edge of their tumor.

The method is based on a large-area tissue field image 27, typically showing a tissue region of several centimeters square, recorded by the surgical microscope 1, that is to say by at least one of its image sensors. The tissue field image 27 may also have a moderate magnification, typically ranging between 5× and 40×. Moreover, at least one histology image 29 is recorded by means of the endomicroscope 3 within the scope of the method, the tumor cell proportion, that is to say the proportion of tumor cells 30 in the totality of cells in the tissue segment 36 depicted in the histology image, being determined on the basis of said histology image in the present exemplary embodiment. In the present exemplary embodiment, the computer 5 carries out a method on the basis of these images, the tissue field image 27 being processed with the aid of said method, in such a way that the edge of the tumor is emphasized in said tissue field image. In FIG. 5, the emphasis is implemented by virtue of emphasizing the image regions where the intensity of the fluorescence radiation has a certain characteristic. These regions typically form the marking line 21 which encloses a tissue region considered to be tumor tissue.

In the present exemplary embodiment, determining the characteristic and processing the tissue field image 27 obtained by the surgical microscope 1 is implemented with the aid of a computer program run on the computer 5. However, rather than running on the computer 5, the computer program can also be run on any other data processing system, for example on a data processing system integrated in the surgical microscope 1. The steps carried out by the method implemented by the computer program are depicted in FIG. 4 as a flowchart.

In a first step S1 of the method, the computer 5 receives the not yet processed tissue field image 27 from the surgical microscope 1 or its image sensors. Moreover, in the present exemplary embodiment, the computer 5 receives in step S2 a specified value for the tumor cell proportion, that is to say a specified proportion of tumor cells 30 in the totality of cells of a tissue region, the tissue attaining or exceeding said proportion being intended to be considered as tumor tissue. Below, this value is referred to as specified tumor cell proportion. However, a value for a different quantifiable histological information item may be specified instead of the tumor cell proportion. By way of example, should a low-oxygen region of the tumor, that is to say a region in which the oxygen content of the tumor cells does not exceed a certain value, be marked, it is possible to specify a value for the oxygen content of the tumor cells which is intended to represent the limit of the low-oxygen region. The computer 5 can receive the tumor cell proportion or optionally a value for a different quantifiable histological information item by way of an input via the keyboard 7, by way of a voice input, by way of a reception from a network, by way of reading a computer-readable storage medium, etc. However, there is also the option of a value for the specified tumor cell proportion being stored in the computer program itself. However, it is advantageous in this case if the stored specified tumor cell proportion can be altered by entering, reading or receiving an alternative specified tumor cell proportion. The specified tumor cell proportion may be situated in the range between 5% and 30%. It is typically situated in the range from 5% to 15% and can be 10%, for example.

Then, an actual tumor cell proportion or optionally an actual value of a different quantifiable histological information item is provided in step S3 for a tissue segment 36 of the tissue region 25 depicted in an image portion of the tissue field image 27. In the present exemplary embodiment, this tissue segment 36 is a part of the tissue region 25 for which a histology image 29 has been recorded by means of the endomicroscope 3. In the present exemplary embodiment, the histology image 29 is used to determine the actual tumor cell proportion of the tissue segment depicted in the histology image 29, that is to say the tumor cell proportion actually present in this tissue segment. By way of example, the actual tumor cell proportion can be determined on the basis of the cell morphology. By way of example, the cell structure or the size of the nucleus can be used as criteria, on the basis of which tumor cells 30 can be distinguished from healthy tissue cells 32. Alternatively, there is the option of determining the tumor cell proportion with the aid of a fluorescence method. By way of example, the number of fluorescing cells can be determined in the histology image 29. Furthermore, there is the option of carrying out a biopsy and determining the tumor cell proportion by means of conventional rapid section histology, with the taken material also being able to be stained. In principle, it is also possible to determine the tumor cell proportion for the tissue segment 36 prior to surgery, for example by means of magnetic resonance imaging. However, the location for which the tumor cell proportion has been determined must in this case be placed so that it is located in the region of the tissue field image 27, and must be marked so that it can be found with the aid of a navigation system during the operation. Optionally, values of other quantifiable histological information items may also be determined with the aid of the described methods.

The actual tumor cell proportion can be determined directly before the provision of the actual tumor cell proportion in step S3, for example with the aid of a program module which is integrated in the computer program and which is designed to distinguish between tumor cells 30 and healthy tissue cells 32 in the histology image 29, for example on the basis of morphological criteria or on the basis of a fluorescence signal emanating from the tumor cells, and which is moreover designed to determine the component of the identified tumor cells 30 in the totality of the cells to be identified in the histology image 29 and provide this as the actual tumor cell proportion. Alternatively, the actual tumor cell proportion may also be determined a relatively long time before the provision of the actual tumor cell proportion in step S3, for example should this be implemented presurgery as mentioned above.

Then, an actual intensity value for the intensity of the fluorescence radiation is determined in step S4 for the image portion of the tissue field image 27 that forms the tissue segment 36 depicted in the histology image 29. If the fluorescent dye is chosen in such a way that the fluorescence intensity at a point in the tissue field image 27 correlates with the tumor cell proportion at this point, and moreover if the fluorescence in the histology image 29 facilitates the determination of the tumor cell proportion, determining the actual tumor cell proportion and determining the actual intensity value can be implemented directly in succession with the aid of the same fluorescent dye. In principle, these demands are met in the case of Blue 400™ since the fluorescence intensity of PpIX correlates with the tumor cell proportion and since PpIX accumulates in the tumor cells so that it can be used for the identification of tumor cells in the histology image 29.

Once the actual tumor cell proportion has been provided in step S3 and the actual intensity value of the fluorescence has been determined in step S4, these two variables are used in step S5 for determining the value of the fluorescence intensity at the specified tumor cell proportion. In the present exemplary embodiment, the value of the fluorescence intensity at the specified tumor cell proportion is determined on the basis of a calculation.

In the fluorescent dye PpIX used in the present exemplary embodiment, the correlation between the change in the fluorescence intensity on the one hand and the change in the tumor cell proportion on the other hand is known. That is to say, the extent to which the fluorescence signal changes when the tumor cell proportion changes by a certain amount is known. If the value of the fluorescence intensity is now known for a certain tumor cell proportion, the value of the fluorescence intensity for other tumor cell proportions can also be calculated on the basis of this correlation. The actual intensity value for the actual tumor cell proportion has been determined in the present exemplary embodiment. The corresponding value of the fluorescence intensity can therefore be calculated on the basis of the correlation for the specified tumor cell proportion. This calculated value of the fluorescence intensity is finally defined in step S6 as the characteristic for the fluorescence intensity that should mark the edge of the tumor. In this way, a fluorescence intensity value for a specified tumor cell proportion of 10%, for example, can be calculated if the actual intensity value associated with any actual tumor cell proportion has been determined.

Finally, in step S7, the edge of the tumor 23 is marked in the tissue field image on the basis of the characteristic, for example by virtue of highlighting the image regions where the fluorescence intensity has the characteristic. The corresponding image regions then form the marking line 21 shown in FIG. 5. Image regions located within the marking line 21 correspond to a tumor cell proportion higher than specified while image regions outside of the boundary correspond to a lower tumor cell proportion. Since the specified tumor cell proportion is chosen in such a way that it is intended to mark the edge of the tumor 23, these regions within the marking line 21 represent the tumor 23 and the regions outside of the marking line 21 represent tissue to be preserved when the tumor is removed.

Since the actual tumor cell proportion and the actual intensity are determined on the basis of the current tumor 23 in the current patient, the described method facilitates the individual determination of the edge of the tumor 23 for a patient.

The procedure according to the first exemplary embodiment requires a known correlation between the change in the fluorescence intensity on the one hand and the change in the tumor cell proportion on the other hand. However, even if such a correlation is unknown or too complex, the edge of a tumor can be determined on the basis of the fluorescence intensity and on the basis of a histology image 29. The corresponding procedure is explained below on the basis of a second exemplary embodiment of the invention, with reference being made to the flowchart depicted in FIG. 7.

In the second exemplary embodiment, the tissue field image is received from the surgical microscope 1 in step S11, as was described in relation to step S1 of FIG. 4.

A specified tumor cell proportion which is intended to mark the edge of the tumor 23 is defined in step S12. The procedure in step S12 also corresponds the procedure from the first exemplary embodiment, that is to say the procedure from step S2.

Then, the actual tumor cell proportion is determined in step S13 for a tissue segment 36 of the tissue region 25 depicted in the tissue field image 27. In this case, the tumor cell proportion can in principle be determined using the same methods as described in relation to step S3 in the first exemplary embodiment.

Then, a check as to whether the tumor cell proportion determined in step S13 corresponds to the specified tumor cell proportion is carried out in step S14 of the second exemplary embodiment on the basis of a comparison between the tumor cell proportion determined in step S13 and the specified tumor cell proportion. According to the present exemplary embodiment, the determined actual tumor cell proportion corresponds to the specified tumor cell proportion if its value is situated within a specified tolerance range around the specified tumor cell proportion, for example within a tolerance range of ±10% around the specified tumor cell proportion or within a tolerance range of ±5% around the specified tumor cell proportion, with the limits of the tolerance range however not necessarily needing to be symmetrical about the specified tumor cell proportion. By way of example, if a tumor cell proportion of 10% is specified, the actual tumor cell proportion, depending on the sharpness of the tolerance range, may be considered to be corresponding to the specified tumor cell proportion if it is located, for example, in the range from 9% to 11%, in the range from 9.5% to 10.5%, in the range from 9% to 10.5%, etc. Different tolerance ranges can be used depending on tumor type and patient.

Should the actual tumor cell proportion be determined as not corresponding to the specified tumor cell proportion, that is to say should the value of the actual tumor cell proportion not be situated within the tolerance range around the specified tumor cell proportion, in step S14, the method advances to step S15, in which a different tissue segment 36' of the tissue region 25 imaged in the tissue field image 27 is selected. Then, the method returns to step S13, in which the actual tumor cell proportion is determined for the new tissue segment 36'. Steps S13, S14 and S15 are carried out until a tissue segment 36' has been found, for which the actual tumor cell proportion is determined in step S14 as corresponding to the specified tumor cell proportion, that is to say the actual tumor cell proportion is situated within the tolerance limits around the specified tumor cell proportion. The method then advances to step S16.

In step S16, the image portion of the tissue field image 27 in which the actual tumor cell proportion determined for the tissue segment 36' depicted therein corresponds to the specified tumor cell proportion is selected, and the actual intensity value of the fluorescence intensity is determined for this selected image portion. Since the actual tumor cell proportion for this image portion corresponds to the specified tumor cell proportion, the determined actual intensity already represents the fluorescence intensity in the case of the given tumor cell proportion. Therefore, the second exemplary embodiment does not require a calculation of the fluorescence intensity for the specified tumor cell proportion.

In step S17, the actual intensity value determined in step S16 is defined as the characteristic for the fluorescence intensity that marks the edge of the tumor 23. Finally, the edge of the tumor 23 is emphasized with the aid of this characteristic in step S18, as has been described in relation to step S17 of the first exemplary embodiment.

In comparison with the method in the first exemplary embodiment, the method in the second exemplary embodiment requires more time since, as a rule, a greater number of histology images, for each of which the actual tumor cell proportion needs to be determined, are recorded in this than in the first exemplary embodiment. In return, however, no knowledge is required about a correlation between the fluorescence intensity and the tumor cell proportion.

Like in the first exemplary embodiment, a value for another quantifiable histological information item can be specified instead of the tumor cell proportion in the second exemplary embodiment as well. Then, an actual value of this other quantifiable histological information item is determined in step S13 instead of the actual tumor cell proportion.

A third exemplary embodiment is described below with reference to the flowchart with steps S21 to S29 depicted in FIG. 8. In the third exemplary embodiment, steps S21, S22, and S23 correspond to the steps S11, S12, and S13 of the second exemplary embodiment. Moreover, step S26 is identical to step S15 of the second embodiment, step S27 is identical to step S16 of the second embodiment, step S28 is identical to step S17 of the second embodiment, and step S29 is identical to step S18 of the second embodiment. Therefore, the main difference between the third exemplary embodiment and the second exemplary embodiment lies in the fact that there is no automated check as to whether the determined actual tumor cell proportion corresponds to the specified tumor cell proportion. Instead, the actual tumor cell proportion is displayed on the monitor of the computer 5 or any other monitor or display in step S24. Optionally, the histology image 29, on the basis of which the displayed actual tumor cell proportion has been determined, may also be displayed on the monitor or the display in the process. In this case, the user has the option of generating a trigger signal, for example by pressing a key or by way of a voice input, when they are of the opinion that a suitable actual tumor cell proportion is present.

In step S25, the software checks for the presence of a trigger signal after a predetermined time interval has elapsed. Should this not be the case, the method advances to step S26, in which a different tissue segment 36' of the tissue region 25 depicted in the tissue field image 27 is selected. Then, the method returns to step S23, in which the actual tumor cell proportion is determined for the new tissue segment 36'. Steps S23, S24, S25, and S26 are carried out until a trigger signal is present. The method continues with steps S27, S28, and S29 as soon as a trigger signal is available.

In a first modification of the third exemplary embodiment, the tissue field image 27 with the marking line 21 which would arise from the actual tumor cell proportion determined in step S13 is displayed instead of the histology image 29 or in addition to the histology image 29. To this end, steps S27 to S29 are carried out after step S23 and before step S24 in the modification of the third exemplary embodiment so that the tissue field image 27 with the marking line 21 can be displayed in step S24.

In a second modification of the third exemplary embodiment, step S23 of determining the actual tumor cell proportion is dispensed with. Then, only the histology image 29 is displayed in step S24. On the basis of the displayed histology image 29, a pathologist can make an assessment regarding the histological information item, contained in the histology image 29, for the depicted tissue segment 36. If, on the basis of the histological information item, the histologist is of the view that the tissue segment 36 represented in the histology image 29 represents the edge of the tumor, they can generate the trigger signal, whereupon the method continues with steps S27 to S29. Otherwise the method advances to step S26, in which another tissue segment 36' of the tissue region 25 imaged in the tissue field image 27 is selected, and then returns to step S24 in order to display the histology image 29 for this tissue segment 36'.

In the third exemplary embodiment and its modifications, there also is the option of initially recording histology images 29 for a plurality of different tissue segments 36, 36' and/or determining the associated actual tumor cell proportions, and of then displaying the histology images 29 and/or the determined actual tumor cell proportions in step S24. In this case, the computer program offers a selection option, with the aid of which one of the histology images 29 or one of the actual tumor cell proportions can be selected. The selection then leads to the generation of a trigger signal which causes steps S27 to S29 to be carried out on the basis of the selected histology image 29 or on the basis of the histology image 29 that forms a basis for the selected actual tumor cell proportion. For selection purposes, the computer program may for example display a pointer on the monitor, which pointer is placed on a histology image or an actual tumor cell proportion. The selection can then be implemented by means of pressing a key or by means of voice input. Alternatively, there is the option of providing the displayed actual tumor cell proportions or the displayed histology images with numbers or other identifiers. Selection and triggering then can be implemented by entering the identifier assigned to the selected actual tumor cell proportion or to the selected histology image.

Like in the first and second exemplary embodiments, a value for another quantifiable histological information item can be specified instead of the tumor cell proportion in the third exemplary embodiment as well. Then, an actual value of this other quantifiable histological information item is determined in step S23 instead of the actual tumor cell proportion.

The fluorescence intensity can be corrected on the basis of certain criteria in the exemplary embodiments. By way of example, there is the option of determining certain tissue properties, for example by recording an image using white-light illumination, in order to determine specular reflections, for instance, and to accordingly correct the fluorescence intensity in the tissue field image 27. Furthermore, there is the option of determining the topography of the tissue region 25 and taking account of its effects on the representation of the fluorescence image. There likewise is the option of taking account of equipment parameters of the surgical microscope 1, for instance the intensity of the illumination light that excites the fluorescence, the illumination angle, the setting of the magnification interchanger, the focus setting, the intensity attenuation by inserted filters, etc., and of accordingly correcting the fluorescence intensity in the recorded tissue field image 27. All these corrections serve to determine the true fluorescence intensity, which is influenced by the aforementioned processes, in order thus to facilitate a more precise determination of the characteristic. By way of example, the change in the focus may lead to a change in the work distance, which in turn has effects on the fluorescence intensity captured by the image sensors of the surgical microscope 1. The effects of the illumination intensity are immediately evident, just like the effects of filters introduced into the beam path. There is also a change in the influence on the fluorescence intensity at the individual pixels of the sensors in the case of a change in the magnification since the fluorescence intensity of an object section is distributed among a different number of pixels in the case of different magnification settings.

The present invention has been described in detail on the basis of exemplary embodiments for explanatory purposes. However, a person skilled in the art recognizes that they can deviate from the exemplary embodiments without departing from the scope of the invention. In the case of fluorescence methods, it is possible to use different fluorescence dyes to PpIX. By way of example, a peptide ligand (chlorotoxin), which specifically binds to tumor cells, in particular glioblastoma cells, and which can be provided with a dye fluorescing in the near infrared, is also suitable. A corresponding method is described in Y. Jiang et al.: "*Calibration of fluorescence imaging for tumor surgical margin delineation: multistep registration of fluorescence and histological images*", Journal of Medical Imaging 6(2), 025005 (April to June 2019). Moreover, rather than using fluorescent dyes, the tumor tissue can also be identified in a different way. By way of example, a multispectral sensor or a hyperspectral sensor can be used instead of a conventional image sensor. Such sensors allow the identification of typical spectral signatures of tumor tissue. Fluorescence caused by dyes is no longer required in that case. Instead of the fluorescence intensity, it is then the intensity of certain spectral signatures that is determined for the specified tumor cell proportion. Unlike fluorescence, which is based on an emission of light, the spectral signature is based on a reflection of light. Moreover, there is the option in the described exemplary embodiments of determining the characteristic on the basis of the temporal decay behavior of the intensity, in particular on the basis of the temporal decay behavior of fluorescence radiation, rather than on the basis of the intensity. Therefore, the present invention is not intended to be limited by the exemplary embodiments but rather only by the appended claims.

LIST OF REFERENCE SIGNS

- 1 Surgical microscope
- 3 Endomicroscope
- 5 Computer
- 7 Keyboard
- 9 Optical fiber
- 11 Input end
- 13 Output end
- 15 Observation object
- 17 Scanning device
- 19 Sensor
- 21 Marking line
- 23 Tumor
- 25 Tissue region
- 27 Tissue field image
- 29 Histology image
- 30 Tumor cells
- 31 Red fluorescing region
- 32 Tissue cells
- 33 Blue background
- 35 Transition range
- 36, 36' Tissue segment

The invention claimed is:

1. A computer-implemented method comprising:

marking a boundary of a tumor in a tissue field image which shows a tissue region with a tumor and which has been obtained by light reflected or emitted by the tissue region, the boundary of the tumor being marked in the tissue field image based on a characteristic for an intensity or a temporal intensity profile of at least one constituent part of the light reflected or emitted by the tissue region, wherein the characteristic is determined based on the intensity or the temporal intensity profile of the at least one constituent part in an image portion, the image portion being a sub-portion of the tissue field image, the image portion corresponding to a tissue segment of the tissue region from which at least one histological information item is determined based on at least one histology image recorded at the image portion and applied to the tissue field image entirely.

2. The computer-implemented method as claimed in claim 1, wherein the at least one histological information item is contained in the at least one histology image recorded at the image portion of the tissue field image.

3. The computer-implemented method as claimed in claim 2, wherein, for determining the characteristic, a plurality of histology images is displayed, the method further comprising:

providing a selection function for selecting a histology image from the displayed plurality of histology images, and determining an actual intensity value or an actual temporal intensity profile for the image portion that shows the tissue segment at which the histology image was recorded, wherein said actual intensity value or said actual temporal intensity profile is configured for determining the characteristic.

4. The computer-implemented method as claimed in claim 2, wherein, for determining the characteristic, the method further comprising:

processing the at least one histological information item contained in the at least one histology image, displaying the at least one histological information item for each of the at least one histology image, and providing a selection function for selecting a selected processed histological information item from the displayed processed histological information items, and determining an actual intensity value or an actual temporal intensity profile for the image portion that shows the tissue segment at which the histology image forming the basis for the selected processed histological information item was recorded, wherein said actual intensity value or said actual temporal intensity profile is defined as the second intensity or the second temporal intensity profile, respectively, for determining the characteristic.

5. The computer-implemented method as claimed in claim 2, wherein an actual intensity value or an actual temporal intensity profile is determined in relation to each recorded histology image for the image portion of the tissue field image that corresponds to the tissue segment depicted in the histology image, and image regions in which a value of an intensity or a temporal intensity profile of the light that corresponds to the respectively determined actual intensity value or the respectively determined actual temporal intensity profile are marked in the tissue field image.

6. The computer-implemented method as claimed in claim 1, wherein the at least one histological information item is a quantifiable histological information item, and an actual value of the quantifiable histological information item and a specified value for the quantifiable histological information item which should mark the boundary of the tumor are used for determining the characteristic.

7. The computer-implemented method as claimed in claim 6, wherein the quantifiable histological information item is the tumor cell proportion, the actual value of the quantifiable histological information item is an actual value of the tumor cell proportion, and the actual value of the tumor cell proportion is determined based on at least one received histology image, by virtue of:

tumor cells being identified in the received histology image, and the actual value of the tumor cell proportion for the at least one received histology image is determined based on a number of identified tumor cells.

8. The computer-implemented method as claim in claim 6, wherein, for determining the characteristic, the method further comprising:

determining an actual intensity value or an actual temporal intensity profile of the at least one constituent part for the image portion of the tissue field image that corresponds to the tissue segment for which the actual value of the quantifiable histological information item has been obtained;

calculating a value for the intensity or the temporal intensity profile of the at least one constituent part as the specified value for the quantifiable histological information item based on a dependence of the value of the intensity or of the temporal intensity profile of the at least one constituent part on the value of the quantifiable histological information item proceeding from the actual value of the quantifiable histological information item determined for the tissue segment and the actual intensity value determined for the image portion of the tissue field image corresponding to this tissue segment or the actual temporal intensity profile determined for the image portion of the tissue field image corresponding to this tissue segment, and defining the calculated value for the intensity or the temporal intensity profile of the at least one constituent part as the specified value for the quantifiable histological information item as the characteristic.

9. The computer-implemented method as claimed in claim 6, wherein, for determining the characteristic, the method further comprising:

receiving histology images and determining actual values of the quantifiable histological information item for the tissue segments depicted in the received histology images until a tissue segment has been found for which the actual value of the quantifiable histological information item corresponds to the specified value for the quantifiable histological information item, the tissue segments being located in the tissue region depicted in the tissue field image;

selecting the image portion that represents the tissue segment in which the actual value of the quantifiable histological information item corresponds to the specified value for the quantifiable histological information item; and determining the actual intensity value or the actual temporal intensity profile of the intensity of the at least one constituent part for the selected image portion, wherein the characteristic is determined based on defining the actual intensity value or the actual temporal intensity profile of the selected image portion as the intensity or the temporal intensity profile, respectively, of the at least one constituent part.

10. The computer-implemented method as claimed in claim 1, wherein the tissue field image is a fluorescence image and the at least one constituent part is at least one spectral line of fluorescence radiation emitted by the tissue region.

11. The computer-implemented method as claimed in claim 1, wherein a correction of a value of an actual intensity or of an actual temporal intensity profile of the at least one constituent part is implemented based on at least one of data records contained in the following group: a data record representing reflection properties of the tissue region, a data record representing topography of the tissue region, a data record representing at least one equipment parameter of a recording apparatus used to record the tissue field image.

12. A method for producing a processed tissue field image of a tissue region with a tumor, in which a boundary of the tumor is marked, the method comprising the steps of:

obtaining at least one histological information item for at least one tissue segment of the tissue region;

recording a tissue field image of the tissue region; and carrying out the computer-implemented method as claimed in claim 1 based on the obtained at least one histological information item and the recorded tissue field image, the tissue field image with the marked boundary of the tumor forming the processed tissue field image.

13. The method as claimed in claim 12, wherein a fluorescence image is recorded as the tissue field image, with the at least one constituent part being at least one spectral line of fluorescence radiation emitted by the tissue region.

14. The method as claimed in claim 12, wherein a histology image containing the at least one histological information item is recorded for obtaining the at least one histological information item.

15. The method as claimed in claim 12, wherein coordinates of the tissue segment from which the at least one histological information item is obtained are stored, and a recording apparatus used to record the tissue field image is aligned by a navigation system so that the tissue segment from which the at least one histological information item has been obtained is imaged in an image portion of the tissue field image.

16. The method as claimed in claim 12, wherein the tissue field image is recorded by a surgical microscope and/or the histology image is recorded by an endomicroscope.

17. The method as claimed in claim 12, wherein an actual intensity used to determine the characteristic or an actual temporal intensity profile used to determine the characteristic is determined with the aid of an endomicroscope.

18. The method as claimed in claim 16, wherein the surgical microscope comprises a hyperspectral sensor or a multispectral sensor and/or the endomicroscope comprises a hyperspectral sensor or a multispectral sensor.

19. A non-volatile computer-readable storage medium with instructions stored thereon for marking a boundary of a tumor in a tissue field image which shows a tissue region with a tumor and which has been obtained by light reflected or emitted by the tissue region, comprising instructions which, when executed on a computer, cause the computer to perform the method of claim 1.

20. A data processing system having a processor and at least one memory, with the processor being configured to execute computer-readable instructions stored on the memory that cause the computer to perform the method of claim 1.

21. A medical apparatus for producing a processed tissue field image of a tissue region with a tumor, in which a boundary of the tumor is marked, comprising:

a surgical microscope for recording a tissue field image of the tissue region with the tumor;

an endomicroscope for recording a histology image or an interface for receiving at least one histological information item which has been determined for a tissue segment of the tissue region depicted in an image portion of the tissue field image, and/or for receiving at least one histology image; and a data processing system as claimed in claim 20.

22. The medical apparatus as claimed in claim 21, further comprising a light source having a spectral characteristic that is able to induce a fluorescence in the tissue region.

* * * * *